(12) United States Patent
Reich et al.

(10) Patent No.: US 8,934,091 B2
(45) Date of Patent: Jan. 13, 2015

(54) MONITORING INCIDENT BEAM POSITION IN A WAFER INSPECTION SYSTEM

(71) Applicant: KLA-Tencor Corporation, Milpitas, CA (US)

(72) Inventors: Juergen Reich, Campbell, CA (US); Aleksey Petrenko, Milpitas, CA (US); Richard Fong, Sunnyvale, CA (US); Bret Whiteside, Gilroy, CA (US); Jien Cao, Fremont, CA (US); Christian Wolters, Campbell, CA (US); Anatoly Romanovsky, Palo Alto, CA (US); Daniel Kavaldjiev, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 123 days.

(21) Appl. No.: 13/794,030

(22) Filed: Mar. 11, 2013

(65) Prior Publication Data
US 2014/0071437 A1   Mar. 13, 2014

Related U.S. Application Data

(60) Provisional application No. 61/698,717, filed on Sep. 9, 2012.

(51) Int. Cl.
*G01J 1/00* (2006.01)
*H01L 21/67* (2006.01)
*G01J 1/42* (2006.01)

(52) U.S. Cl.
CPC .................................. *G01J 1/4257* (2013.01)
USPC .......................................... 356/121; 356/620

(58) Field of Classification Search
CPC ....................................................... H01L 21/67
USPC ................................................... 356/121, 620
See application file for complete search history.

(56) References Cited

U.S. PATENT DOCUMENTS

| | | | |
|---|---|---|---|
| 5,189,481 A | | 2/1993 | Jann et al. |
| 6,342,705 B1 * | | 1/2002 | Li et al. ........................ 250/559.4 |
| 6,933,738 B2 * | | 8/2005 | Martin et al. ............. 324/750.25 |
| 2003/0013340 A1 * | | 1/2003 | Martin et al. .................. 439/488 |

FOREIGN PATENT DOCUMENTS

| | | |
|---|---|---|
| JP | 11-326229 | 11/1999 |
| JP | 2000-232138 | 8/2000 |
| JP | 2008-066611 | 3/2008 |
| JP | 2011-141184 | 7/2011 |

OTHER PUBLICATIONS

International Search Report and Written Opinion for PCT/US2013/058569 mailed Dec. 13, 2013.

\* cited by examiner

*Primary Examiner* — Roy M Punnoose
(74) *Attorney, Agent, or Firm* — Ann Marie Mewherter

(57) ABSTRACT

Methods, systems, and structures for monitoring incident beam position in a wafer inspection system are provided. One structure includes a feature formed in a chuck configured to support a wafer during inspection by the wafer inspection system. The chuck rotates the wafer in a theta direction and simultaneously translates the wafer in a radial direction during the inspection. An axis through the center of the feature is aligned with a radius of the chuck such that a position of the axis relative to an incident beam of the wafer inspection system indicates changes in the incident beam position in the theta direction.

22 Claims, 2 Drawing Sheets

MONITORING INCIDENT BEAM POSITION IN A WAFER INSPECTION SYSTEM

BACKGROUND OF THE INVENTION

1. Field of the Invention

This invention generally relates to structures, systems, and methods for monitoring incident beam position in a wafer inspection system.

2. Description of the Related Art

The following description and examples are not admitted to be prior art by virtue of their inclusion in this section.

Inspection processes are used at various times during a semiconductor manufacturing process to detect defects on wafers. Inspection has always been an important part of fabricating semiconductor devices such as integrated circuits. However, as the dimensions of semiconductor devices decrease, inspection becomes even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

Determining the positions of defects on wafers is also important to facilitate processes such as defect review, during which locations on the wafer at which defects are located are re-visited to generate additional information about the defects. Therefore, if the determined defect locations are inaccurate, the defects must be searched for during review, which will reduce the throughput of the review process. In addition, inaccurate defect locations may reduce the accuracy and usefulness of review if other defects happen to be located at the inaccurate locations thereby confusing the results of inspection and review. Obviously, as the size of defects decreases, the acceptable error in the defect location also decreases. For example, the difficulty of finding defects based on inaccurate defect locations increases as the defect size decreases. Inaccurate defect locations will obviously affect any process that is performed based on defect location information such as defect repair or removal, defect analysis, etc.

One method for increasing the accuracy of defect detection and defect position determination is to accurately calibrate the inspection system prior to inspection of a wafer. For instance, during calibration of an inspection system, the offset of the light beam from the center of the chuck on which a wafer will be located during inspection may be measured. The measured offset can then be used to correct positional information acquired during the inspection. Therefore, some calibration processes do account for drift in the light beam with respect to the chuck. However, since the calibration processes are typically not performed frequently (e.g., since frequent calibration will reduce throughput), any drift in the position of the light beam between calibrations is not measured. Instead, the incident light beam position with respect to the chuck is assumed to be relatively stable between calibrations. Therefore, any drift in the position of the light beam between calibrations will produce error in the reported coordinates of defect locations on the wafer.

Accordingly, it would be advantageous to develop methods, systems, and structures for monitoring incident beam position in a wafer inspection system that do not have one or more of the disadvantages described above.

SUMMARY OF THE INVENTION

The following description of various embodiments is not to be construed in any way as limiting the subject matter of the appended claims.

One embodiment relates to a structure configured for monitoring incident beam position in a wafer inspection system. The structure includes a chuck configured to support a wafer during inspection by the wafer inspection system. The chuck rotates the wafer in a theta direction and simultaneously translates the wafer in a radial direction during the inspection. The structure also includes a feature formed in the chuck. An axis through the center of the feature is aligned with a radius of the chuck such that a position of the axis relative to an incident beam of the wafer inspection system indicates changes in the incident beam position in the theta direction.

Another embodiment relates to a method for monitoring incident beam position in a wafer inspection system. The method includes directing an incident beam to a feature formed in a chuck configured to support a wafer during inspection by the wafer inspection system. The chuck rotates the wafer in a theta direction and simultaneously translates the wafer in a radial direction during the inspection. An axis through the center of the feature is aligned with a radius of the chuck such that a position of the axis relative to an incident beam of the wafer inspection system indicates changes in the incident beam position in the theta direction. The method also includes detecting light from the feature due to directing the incident beam to the feature and generating output responsive to the detected light. In addition, the method includes determining the incident beam position in the theta direction based on the output. Determining the incident beam position is performed using a computer system.

The method described above may be performed as described further herein. In addition, the method described above may include any other step(s) of any other method(s) described herein. Furthermore, the method described above may be performed by any of the systems described herein.

Another embodiment relates to a wafer inspection system configured to monitor incident beam position. The system includes a chuck and a feature configured as described above. The system also includes an illumination subsystem configured to scan the incident beam over the feature. In addition, the system includes a detector configured to detect light from the feature due to scanning of the incident beam over the feature and to generate output responsive to the detected light. The system further includes a computer subsystem configured to determine the incident beam position in the theta direction based on the output. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
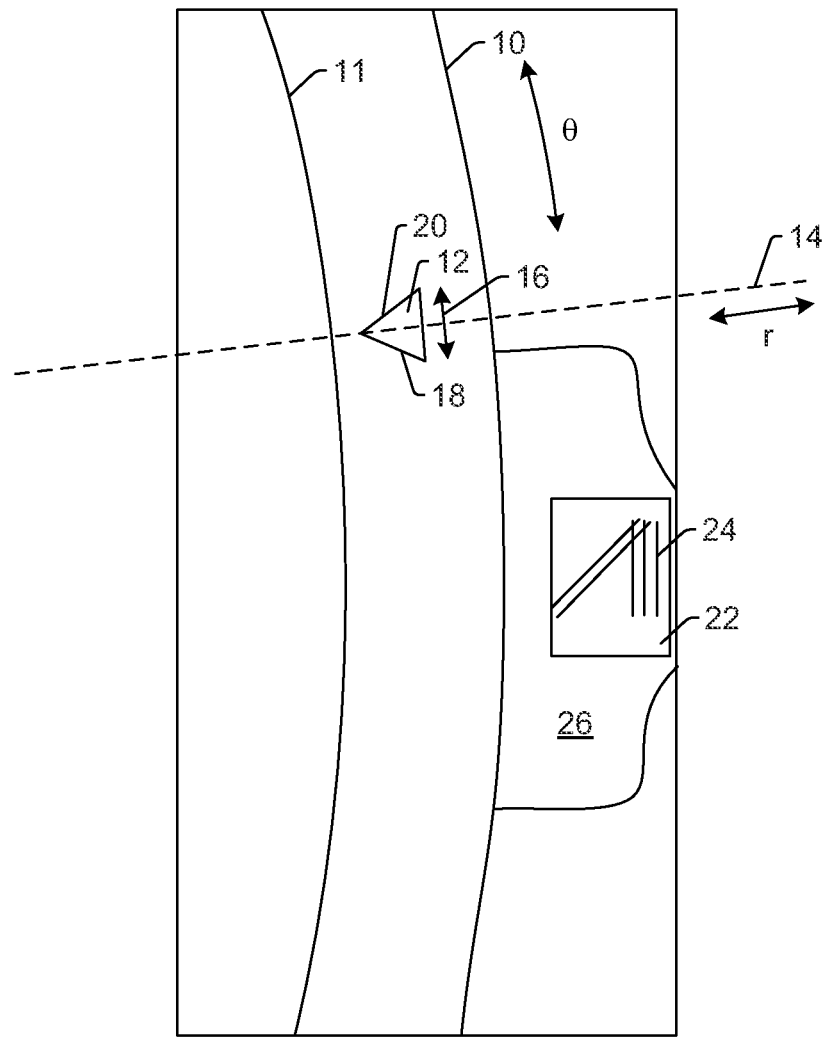
FIG. 1 is a schematic diagram illustrating a plan view of one embodiment of a structure configured for monitoring incident beam position in a wafer inspection system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

In general, the embodiments described herein relate to measuring beam drifts on an inspection system and/or monitoring incident beam drifts in time. One embodiment relates to a structure configured for monitoring incident beam position in a wafer inspection system. The wafer inspection system may be a laser inspection system. The wafer inspection system may be further configured as described herein. The wafer inspection system may be configured such that one or more light beams used by the system to inspect a wafer are stationary white the wafer is moved with respect to the light beam(s) such that the light beam(s) scan over the wafer. In this manner, the embodiments described herein may be used to determine if the position of the stationary light beam(s) has drifted during inspection of the wafer. Such drift in the position of the light beam(s) would be disadvantageous since it would adversely affect any positional information gathered during wafer inspection. Therefore, the embodiments described herein may be used to increase the accuracy of any positional information acquired during wafer inspection.

The structure includes a chuck configured to support a wafer during inspection by the wafer inspection system. For example, as shown in FIG. 1, the structure may include chuck 10 configured to support wafer 11 during inspection by the wafer inspection system (not shown in FIG. 1). The chuck rotates the wafer in a theta direction, θ shown in FIG. 1, and simultaneously translates the wafer in a radial direction, r shown in FIG. 1, during the inspection. For example, the chuck may be coupled to an R-theta stage that is configured to move the chuck such that one or more incident beams can be scanned over the wafer. In this manner, the light beam(s) of the inspection system may scan a spiral path on the wafer during inspection. In particular, in an R-theta scanner, the incident beam is fixed white the wafer is translated in the radial direction and rotated in the theta direction at the same time in order to map out a spiral scan on the wafer. The chuck may include any suitable commercially available chuck that can be modified to include a feature described further herein.

The structure also includes a feature formed in the chuck. For example, as shown in FIG. 1, the structure may include feature 12 formed in chuck 10. In this manner, the feature is built into or integrated into the chuck that is also used for otherwise handling the wafer. An axis through the center of the feature is aligned with a radius of the chuck such that a position of the axis relative to an incident beam of the wafer inspection system indicates changes in the incident beam position in the theta direction. For example, axis 14 of feature 12 may be aligned with a radius of chuck 10. In this manner, in order for the feature to have sensitivity to theta drift, the feature is oriented radially. In particular, in order to measure an incident beam drift in the theta direction, perpendicular to the wafer translation direction, the feature should be aligned radially, meaning parallel to the translation direction. As such, during a scan over the feature, the center of the feature may be recorded for each track in the scan. Incident beam motions in the theta direction show as changes in the center positions. As such, as the chuck rotates under the incident beam, the theta angle of the feature can be measured, the changes in the theta angle over time can be monitored, and those changes indicate a beam motion in the theta direction. The feature may be formed in the chuck using any suitable manufacturing process known in the art.

In one embodiment, a width of the feature varies along the radius of the chuck such that the width measured using the incident beam indicates changes in the incident beam position in the radial direction. For example, in order for the feature to have sensitivity to radial drifts in the incident beam position, the feature can have radially varying width. As shown in FIG. 1, width 16 of feature 12 varies along axis 14 through the center of the feature that is aligned with the radius of the chuck. In this manner, the width of the feature varies along the radius of the chuck. As such, during a scan over the feature, the width of the feature may be measured. Changes in radial pointing of the incident beam show as changes in the width of the feature at a given radius.

In another embodiment, one or more sides of the feature are not parallel or perpendicular to the radius of the chuck such that a width of the feature measured using the incident beam indicates changes in the incident beam position in the radial direction. For example, in order for the feature to have sensitivity to radial drifts in the incident beam position, the feature can be tilted at an angle. In other words, in order to measure and/or monitor the radial position of the incident beam, one or more sides of the feature may have some angle relative to the direction of translation. In one such example, as shown in FIG. 1, sides 18 and 20 of feature 12 are not parallel or perpendicular to the radius of the chuck (that is aligned with axis 14). In this manner, one or more sides of the feature have some angle relative to the translation direction. In this manner, the incident beam drift in the radial direction, parallel to the translation of the wafer, can be measured. Instead, the feature could be arranged perpendicular to the translation axis, the rotary stage may be turned off, and the feature translated in the radial direction under the incident beam while the radial position where the beam is encountered by the feature over time is monitored.

In some embodiments, the feature forms an opening in the chuck. In this manner, as the incident beam scans over the opening, the light transmitted through the opening can be detected below. The feature can have different shapes to be sensitive to radial beam drifts or tangential beam drifts or both. For example, in one embodiment, the feature forms a triangular opening in the chuck. In one such example, as shown in FIG. 1, feature 12 has a triangular shape and may be an opening in the chuck. However, different shapes and types of openings can be used. For example, the opening may have a diamond shape.

In one embodiment, the feature includes a material formed in an opening in the chuck, and the material transmits the incident beam and an additional incident beam of the wafer inspection system such that the feature is configured for monitoring the incident beam position and a position of the additional incident beam. Multiple incident beams may be used to inspect the wafer at different incident angles or different wavelengths. By adjusting the transmission of the feature for different wavelengths, adequate signal levels can be obtained by a detector for different incident beams. As such, to monitor the drifts of more than one incident beam with the same detector, the feature may be designed to be a transparent material with tuned attenuation for the different wavelengths of the incident beams such that the signals are in a useful range for all incident beams even though the incident beams have different power levels. In this manner, the structure can be used for different incident beams. All other embodiments described herein may be used for different incident beams as well. In this manner, the embodiments described herein may be used for one incident beam or multiple beams. In addition, the feature can be used for a beam used to inspect the wafer surface and/or for an additional beam. The additional beam may be, for example, a laser beam used for measuring the wafer edge in parallel to the inspection scan. From this edge scan, the wafer location and orientation inside the tool can be determined. In addition, although the feature may include a material formed in the opening, the feature may also include no material formed in the opening.

In some embodiments, the feature is formed in the chuck such that the incident beam can be scanned over the feature as part of the inspection. For example, as the chuck moves under the incident beam, the beam scans over the feature. On an R-theta system, movement in the radial and theta directions can be used. In addition, since the feature is implemented in the chuck, it can be measured as part of the general wafer scan sequence. In this manner, scanning the feature can be integrated in a regular wafer surface scan and can be faster than scanning of currently used features. However, the feature can also be scanned in a scan separate from the wafer scan.

In one embodiment, the feature is configured to scatter the incident beam. For example, the feature may include one or more elements such as patterned lines etched into the chuck that are configured to scatter or diffract the incident beam. In another embodiment, the feature is configured to reflect the incident beam. For example, a reflective material may be deposited in an opening formed in the chuck by etching such that the reflective material reflects the light beam(s) while the light beam(s) are scanned over the feature. In this manner, instead of an opening such as that described herein, a reflecting and/or scattering feature may be used. As such, the feature can be made to be used with the incident beam being transmitted, reflected, or scattered. Regardless of whether the feature is configured to transmit, reflect, or scatter light, the feature can have shapes such as those described above and may otherwise be configured as described herein such that the features are sensitive to incident beam position drifts in the radial and/or theta directions. The light (either transmitted or reflected or scattered) from the feature can be detected with different detectors. Although detecting either transmitted or reflected or scattered light should be sufficient for monitoring the incident beam position as described herein, it is conceivable that there could be instances in which it would be advantageous to detect some combination of transmitted, reflected, and scattered light from the feature.

As described above, therefore, the structure embodiments described herein are significantly different than structures previously used for monitoring incident beam positions. For example, previously used structures include XY tiles such as XY tile 22 shown in FIG. 1. As shown in FIG. 1, XY tile 22 is a feature having a rectangular shape with lines 24 formed on the feature. The XY tile is mounted separately from the wafer carrying chuck 10. For example, the XY tile is mounted on support 26 that is attached to the chuck. XY tiles provide limited accuracy for measuring drifts perpendicular to the direction of the XY tile scan. In addition, the previously used features are linked to motion in the radial direction only and measurement of beam drift in the theta direction is indirect and imprecise. In the embodiments described herein, the motion is mostly in theta and drifts in theta can be measured more precisely. In particular, the embodiments described herein are more sensitive to tangential beam drifts than previously used structures.

Each of the embodiments of the structure described above may be further configured as described herein. In addition, each of the embodiments of the structure described above may be used in any of the methods described herein. Each of the embodiments of the structure described above may also be included in and used by any of the wafer inspection systems described herein.

Another embodiment relates to a method for monitoring incident beam position in a wafer inspection system. The wafer inspection system may be configured as described further herein. The method includes directing an incident beam to a feature formed in a chuck configured to support a wafer during inspection by the wafer inspection system. Directing the incident beam to the feature may include scanning the incident beam over the feature such that the incident beam illuminates the feature. Scanning the incident beam over the feature may be performed in a manner similar to scanning the incident beam over the wafer with adjustments made to the scanning due to positional differences between the wafer and the feature.

The chuck and the feature used in the method are configured as described above. For example, the chuck rotates the wafer in a theta direction and simultaneously translates the wafer in a radial direction during the inspection. An axis through the center of the feature is aligned with a radius of the chuck such that a position of the axis relative to an incident beam of the wafer inspection system indicates changes in the incident beam position in the theta direction. Such a chuck and feature may be further configured as described herein.

In one embodiment, directing the incident beam to the feature includes scanning the incident beam over the feature as part of the inspection. For example, scanning for inspection involves scanning incident beam(s) over the wafer as described herein. Therefore, before or after the incident beam(s) are scanned over the wafer, the incident beam(s) can be scanned over the feature in one single scan path (e.g., without stopping and restarting the scan). As such, the feature can be scanned in the methods described herein quicker than in previously used methods for monitoring incident beam position.

The method also includes detecting light from the feature due to directing the incident beam to the feature and generating output responsive to the detected light. Detecting the light from the feature may be performed using a detector such as that described further herein. The output generated by the detector may include any suitable output such as signals, images, image data, data, and the like.

In one embodiment, the light from the feature includes light transmitted by the feature. In another embodiment, the light from the feature includes light scattered by the feature. In an additional embodiment, the light from the feature includes light reflected by the feature. For example, the feature may be configured as described herein to transmit, scatter, or reflect light depending on the configuration of the feature.

The method further includes determining the incident beam position in the theta direction based on the output. For example, as described further herein, determining the incident beam position in the theta direction may include determining a position of the center (or the axis through the center) of the feature that is aligned with the radius of the chuck along which the wafer is translated using the output generated by the detector. More specifically, the width of the feature can be determined using the output generated by the detector during scanning of the incident beam over the feature in any suitable manner, and then the center position (or the position of the axis through the center) of the feature can be determined from the width. The position of the center (or the axis through the center) relative to the radius of the chuck along which the wafer is translated may then be determined and indicates the position of the center (or the axis through the center) in the theta direction. Any distance between the position of the center (or the axis through the center) and the radius of the chuck along which the wafer is translated may indicate that the incident beam position has drifted in the theta direction.

Determining the incident beam position is performed using a computer system, which may be configured as described further herein.

The feature and the chuck may be further configured as described herein. For example, in one embodiment, a width of the feature varies along the radius of the chuck such that the width measured using the incident beam indicates changes in the incident beam position in the radial direction. Such a feature may be further configured as described herein. In one such embodiment, the method includes determining the incident beam position in the radial direction based on the output. For example, since the width of the feature varies along the radius of the chuck in a known manner, the width of the feature may be measured as described above using output generated by the detector during scanning of the incident beam over the feature. The measured width may then be compared to the known width variations to determine the position along the radius at which the width was measured. The determined position then indicates the position of the incident beam in the radial direction.

In another such embodiment, directing the incident beam to the feature and detecting light from the feature include scanning the incident beam over the feature in the theta direction at different positions along the radius of the chuck, and determining the incident beam position in the radial direction includes determining the width of the feature as a function of the different positions along the radius. For example, for robust measurements, the increase (e.g., a linear increase) in width of the feature may be measured versus radial position as described above and a fit over several tracks may be used. In this manner, the feature can be scanned once or multiple times for more accurate measurements.

In one embodiment, the feature includes a material formed in an opening in the chuck, the material transmits the incident beam and an additional incident beam of the wafer inspection system, and the position of the axis relative to the additional incident beam indicates changes in a position of the additional incident beam in the theta direction. Such a feature may be further configured as described herein.

In one such embodiment, the method includes directing the additional incident beam to the feature, detecting light from the feature due to directing the additional incident beam to the feature and generating additional output responsive to the light from the feature due to directing the additional incident beam to the feature, and determining a position of the additional incident beam in the theta direction based on the additional output. These steps may be performed as described further herein with respect to the incident beam.

In another such embodiment, a width of the feature varies along the radius of the chuck such that the width measured using the incident beam indicates changes in the position of the incident beam in the radial direction and the width measured using the additional incident beam indicates changes in the position of the additional incident beam in the radial direction. Such a feature may be further configured as described herein.

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figure 2:
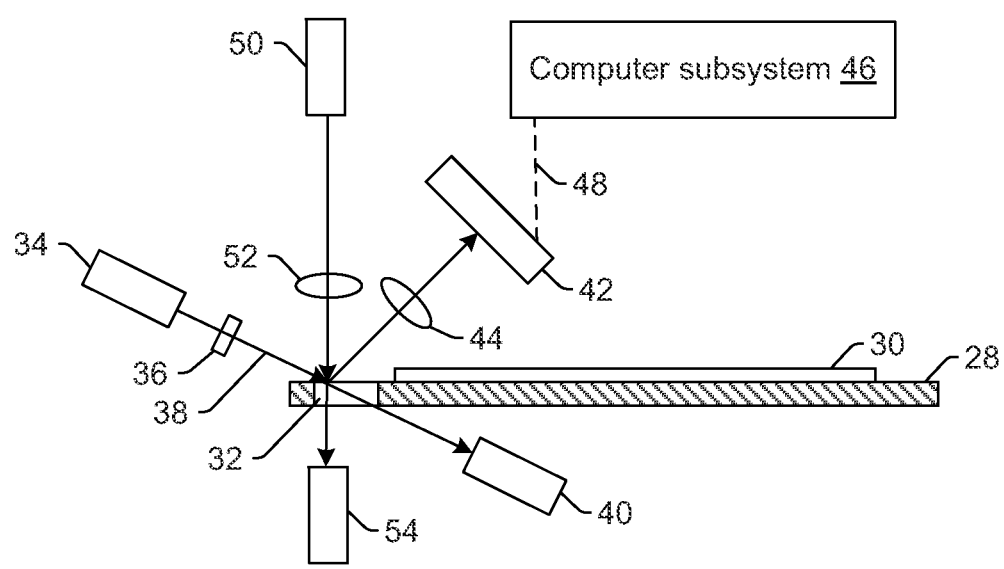
FIG. 2 is a schematic diagram illustrating a side view of one embodiment of a wafer inspection system configured to monitor incident beam position.

An additional embodiment relates to a wafer inspection system configured to monitor incident beam position. One such embodiment is shown in FIG. 2. The wafer inspection system includes a chuck configured to support a wafer during inspection by the wafer inspection system. For example, as shown in FIG. 2, the wafer inspection system includes chuck 28 configured to support wafer 30 during inspection. The chuck rotates the wafer in a theta direction and simultaneously translates the wafer in a radial direction during the inspection. The chuck may be further configured as described herein.

The system also includes a feature formed in the chuck. For example, as shown in FIG. 2, feature 32 may be formed in chuck 28. An axis through the center of the feature is aligned with a radius of the chuck such that a position of the axis relative to an incident beam of the wafer inspection system indicates changes in the incident beam position in the theta direction. Such a feature may be further configured as described herein. For example, in one embodiment, a width of the feature varies along the radius of the chuck such that the width measured using the incident beam indicates changes in the incident beam position in the radial direction. In another embodiment, one or more sides of the feature are not parallel or perpendicular to the radius of the chuck such that a width of the feature measured using the incident beam indicates changes in the incident beam position in the radial direction. Such embodiments of the feature may be further configured as described herein.

The system further includes an illumination subsystem configured to scan the incident beam over the feature. For example, as shown in FIG. 2, the system may include light source 34 and optical element 36 that make up an illumination subsystem. The light source may include any suitable commercially available light source such as a laser. Optical element 36 may include any suitable commercially available optical element such as a polarizer, a spatial filter, a wavelength filter, a lens, and the like. In addition, the illumination subsystem may include more than one optical element (not shown) coupled to the light source. As shown in FIG. 2, the light source may be configured to direct incident beam 38 through optical element 36 to feature 32 formed in chuck 28. The illumination subsystem may scan the incident beam over the feature due to movement by the chuck (e.g., rotation and translation). As shown in FIG. 2, the illumination subsystem may be configured to direct the incident beam to the feature (and the wafer) at an oblique angle of incidence. The oblique angle of incidence may include any suitable oblique angle of incidence and may alternatively be a normal or near normal angle of incidence.

In addition, the system includes a detector configured to detect light from the feature due to scanning of the incident beam over the feature and to generate output responsive to the detected light. For example, in the embodiment shown in FIG.

2, the feature may be transmit the incident beam. As such, the system may include detector 40 configured to detect the light that is transmitted through the feature due to scanning of the incident beam over the feature. Detector 40 may include any suitable commercially available detector such as a photomultiplier tube (PMT) or charge coupled device (CCD). Detector 40 may generate any suitable output responsive to the detected light such as signals, data, image data, and images. As shown in FIG. 2, the detector may be positioned on the side of the chuck opposite to the wafer. Therefore, the detector may not be a detector that is normally used to inspect the wafer and/or is not normally included in currently available wafer inspection systems. However, wafer inspection systems can be easily modified to include such a detector.

In addition, depending on the configuration of the feature, the detector that is used to detect the light from the feature may include a detector that is normally used for inspection of the wafer. For example, if the feature is configured as described further herein to scatter or reflect the incident beam, then the system may include detector 42 that is configured to detect light scattered or reflected from the feature. Such a detector may be further configured as described herein. In addition, such a detector may be used to inspect a wafer. Therefore, the embodiments described herein may use existing elements of currently available wafer inspection systems in order to monitor incident beam positions using the new structures and features described herein.

As further shown in FIG. 2, optical element 44 may be coupled to detector 42. The optical element may include, for example, a lens, a collector, a spectral filter, a polarizing element, and a spatial filter. Such elements may include any suitable commercially available elements known in the art. In addition, more than one such element (not shown in FIG. 2) may be coupled to detector 42. In a similar manner, one or more such elements (not shown) may be coupled to any of the other detectors (e.g., detector 40) described herein.

The system also includes a computer subsystem configured to determine the incident beam position in the theta direction based on the output. For example, as shown in FIG. 2, the system may include computer subsystem 46. The computer subsystem may be coupled to each or any of the detectors described herein (e.g., the computer subsystem may be coupled to detector 42 by transmission medium 48, which may include wired and wireless portions) such that the computer subsystem can receive the output generated by the detectors. The computer subsystem may determine the incident beam position in the theta direction as described further herein. The computer subsystem may also or alternatively determine the incident beam position in the radial direction using the output as described further herein.

The computer subsystem may take various forms, including a personal computer system, image computer, mainframe computer system, workstation, network appliance, Internet appliance, or other device. In general, the term "computer subsystem" may be broadly defined to encompass any device having one or more processors, which executes instructions from a memory medium. The computer subsystem may also include any suitable processor known in the art such as a parallel processor. In addition, the computer subsystem may include a computer platform with high speed processing and software, either as a standalone or a networked tool.

As described further herein, the wafer inspection system may be configured to use more than one incident beam for wafer inspection and/or for other purposes such as inspecting or locating the edge of the wafer. In addition, such incident beams may be directed toward the wafer at different incident angles. Such incident beams may be generated by different light sources. For example, as shown in FIG. 2, the illumination subsystem may include an additional light source 50 that is configured to generate an additional incident beam. As further shown in FIG. 2, light source 50 may be arranged such that the light source directs light to optical element 52, which may include any of the optical elements described further herein, and then to feature 32 at a normal or near normal angle of incidence. In this manner, the incident beam and the additional incident beam may be directed to the feature and to the wafer at different angles of incidence. Such incident beams may also have the same wavelength or different wavelengths. In addition, if the incident beams have one or more different characteristics such as polarization or wavelength, the incident beams may be directed to the feature and the wafer at the same or substantially the same angle of incidence (not shown). Furthermore, the illumination subsystem may be configured such that multiple incident beams are generated from a single light source (either using a light source that generates multiple beams or generating multiple beams, e.g., using a beam splitter, from a single light beam generated by a single light source).

In some embodiments, the same detector, e.g., detector 40, may be configured to detect the light from the feature due to illumination by the incident beam and the additional incident beam. However, the wafer inspection system may also include an additional detector configured to detect only the light from the feature due to illumination by the additional incident beam. For example, as shown in FIG. 2, the wafer inspection system may include detector 54, which may be configured as described herein, to detect light transmitted by feature 32 due to illumination by the additional incident beam. In this manner, the system may include different detectors, each configured to detect light from the feature due to illumination by only one of the incident beams.

It is noted that FIG. 2 is provided herein to generally illustrate one configuration of a wafer inspection system embodiment. Obviously, the inspection system configuration described herein may be altered to optimize the performance of the inspection system as is normally performed when designing a commercial inspection system. In addition, the systems described herein may be implemented using an existing inspection system (e.g., by adding functionality described herein to an existing inspection system). Alternatively, the system described herein may be designed "from scratch" to provide a completely new system.

Each of the system embodiments described above may be further configured according to any of the other embodiment(s) described herein.

Further modifications and alternative embodiments of various aspects of the invention will be apparent to those skilled in the art in view of this description. For example, methods, systems, and structures for monitoring incident beam position in a wafer inspection system are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A structure configured for monitoring incident beam position in a wafer inspection system, comprising:
a chuck configured to support a wafer during inspection by the wafer inspection system, wherein the chuck rotates the wafer in a theta direction and simultaneously translates the wafer in a radial direction during the inspection; and
a feature formed in the chuck, wherein an axis through the center of the feature is aligned with a radius of the chuck such that a position of the axis relative to an incident beam of the wafer inspection system indicates changes in the incident beam position in the theta direction.

2. The structure of claim 1, wherein a width of the feature varies along the radius of the chuck such that the width measured using the incident beam indicates changes in the incident beam position in the radial direction.

3. The structure of claim 1, wherein one or more sides of the feature are not parallel or perpendicular to the radius of the chuck such that a width of the feature measured using the incident beam indicates changes in the incident beam position in the radial direction.

4. The structure of claim 1, wherein the feature forms an opening in the chuck.

5. The structure of claim 1, wherein the feature forms a triangular opening in the chuck.

6. The structure of claim 1, wherein the feature comprises a material formed in an opening in the chuck, and wherein the material transmits the incident beam and an additional incident beam of the wafer inspection system such that the feature is configured for monitoring the incident beam position and a position of the additional incident beam.

7. The structure of claim 1, wherein the feature is formed in the chuck such that the incident beam can be scanned over the feature as part of the inspection.

8. The structure of claim 1, wherein the feature is further configured to scatter the incident beam.

9. The structure of claim 1, wherein the feature is further configured to reflect the incident beam.

10. A method for monitoring incident beam position in a wafer inspection system, comprising:
directing an incident beam to a feature formed in a chuck configured to support a wafer during inspection by the wafer inspection system, wherein the chuck rotates the wafer in a theta direction and simultaneously translates the wafer in a radial direction during the inspection, and wherein an axis through the center of the feature is aligned with a radius of the chuck such that a position of the axis relative to an incident beam of the wafer inspection system indicates changes in the incident beam position in the theta direction;
detecting light from the feature due to said directing and generating output responsive to the detected light; and
determining the incident beam position in the theta direction based on the output, wherein said determining is performed using a computer system.

11. The method of claim 10, wherein a width of the feature varies along the radius of the chuck such that the width measured using the incident beam indicates changes in the incident beam position in the radial direction, and wherein the method further comprises determining the incident beam position in the radial direction based on the output.

12. The method of claim 11, wherein said directing and said detecting comprise scanning the incident beam over the feature in the theta direction at different positions along the radius of the chuck, and wherein said determining the incident beam position in the radial direction comprises determining the width of the feature as a function of the different positions along the radius.

13. The method of claim 10, wherein said directing comprises scanning the incident beam over the feature as part of the inspection.

14. The method of claim 10, wherein the feature comprises a material formed in an opening in the chuck, wherein the material transmits the incident beam and an additional incident beam of the wafer inspection system, and wherein the position of the axis relative to the additional incident beam indicates changes in a position of the additional incident beam in the theta direction.

15. The method of claim 14, further comprising directing the additional incident beam to the feature, detecting light from the feature due to said directing the additional incident beam to the feature and generating additional output responsive to the light from the feature due to said directing the additional incident beam to the feature, and determining a position of the additional incident beam in the theta direction based on the additional output.

16. The method of claim 14, wherein a width of the feature varies along the radius of the chuck such that the width measured using the incident beam indicates changes in the position of the incident beam in the radial direction and the width measured using the additional incident beam indicates changes in the position of the additional incident beam in the radial direction.

17. The method of claim 10, wherein the light from the from the feature comprises light transmitted by the feature.

18. The method of claim 10, wherein the light from the feature comprises light scattered by the feature.

19. The method of claim 10, wherein the light from the feature comprises light reflected by the feature.

20. A wafer inspection system configured to monitor incident beam position, comprising:
a chuck configured to support a wafer during inspection by the wafer inspection system, wherein the chuck rotates the wafer in a theta direction and simultaneously translates the wafer in a radial direction during the inspection;
a feature formed in the chuck, wherein an axis through the center of the feature is aligned with a radius of the chuck such that a position of the axis relative to an incident beam of the wafer inspection system indicates changes in the incident beam position in the theta direction;
an illumination subsystem configured to scan the incident beam over the feature;
a detector configured to detect light from the feature due to scanning of the incident beam over the feature and to the generate output responsive to the detected light; and
a computer subsystem configured to determine the incident beam position in the theta direction based on the output.

21. The system of claim 20, wherein a width of the feature varies along the radius of the chuck such that the width measured using the incident beam indicates changes in the incident beam position in the radial direction.

22. The system of claim 20, wherein one or more sides of the feature are not parallel or perpendicular to the radius of the chuck such that a width of the feature measured using the incident beam indicates changes in the incident beam position in the radial direction.

* * * * *